United States Patent [19]

Bessler et al.

[11] Patent Number: 4,900,143

[45] Date of Patent: Feb. 13, 1990

[54] OPHTHALMOSCOPE HANDPIECE WITH LASER DELIVERY SYSTEM

[75] Inventors: Michael Bessler; Donald P. Hutchinson, both of Knox County, Tenn.

[73] Assignee: Electro-Optics Laboratory, Inc., Anderson County, Tenn.

[21] Appl. No.: 165,718

[22] Filed: Mar. 9, 1988

[51] Int. Cl.$^4$ .............................................. A61B 3/10
[52] U.S. Cl. .................................... 351/205; 351/221; 351/214
[58] Field of Search ............... 351/205, 214, 216, 221; 128/633, 303.1

[56] References Cited

U.S. PATENT DOCUMENTS 3,583,795  6/1971  Heine .................................. 351/221
3,698,099  10/1972  Matsumura ..................... 351/221 X Primary Examiner—Rodney B. Bovernick
Attorney, Agent, or Firm—Pitts and Brittian

[57] ABSTRACT

An ophthalmoscope handpiece (10) for viewing the fundus oculi and for delivering a laser beam and a laser targeting beam to the fundus. The handpiece (10) comprises a body (26) defining a viewing aperture (32) therethrough. The handpiece (10) is provided with magnifying means, including a magnifying lens (38) mounted in the viewing aperture (32) for providing a magnifyied view of the fundus. An optical fiber coupling assembly (46) connects the handpiece (10) to an optical fiber (50) which communicates a laser targeting beam and a laser beam to the handpiece (10). The coupling assembly (46) is received in a receptor (58) provided in the body (26) such that the targeting beam and the laser beam can be directed into the viewing aperture (32) of the handpiece (10). Beam deflecting means (48), mounted within the viewing aperture (32), serves to intercept the laser beam and targeting beam and redirect the beams out of the viewing aperture (32) such that the beams can be directed to the fundus oculi.

7 Claims, 2 Drawing Sheets

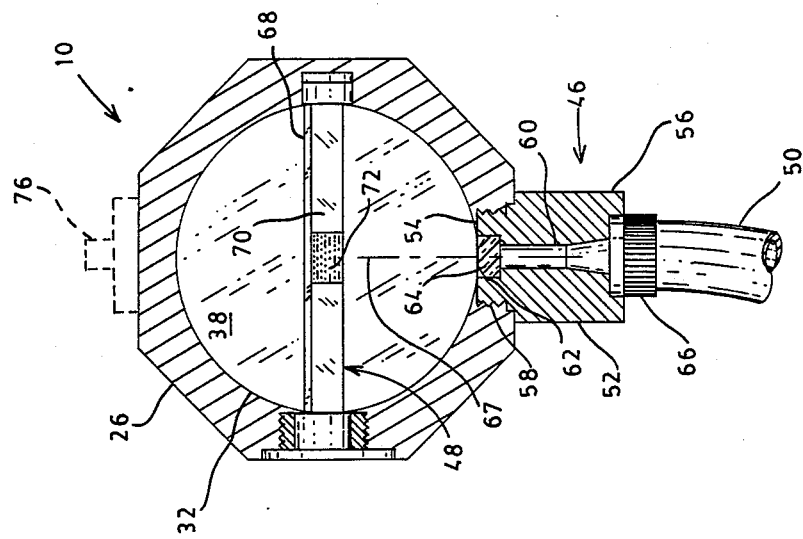
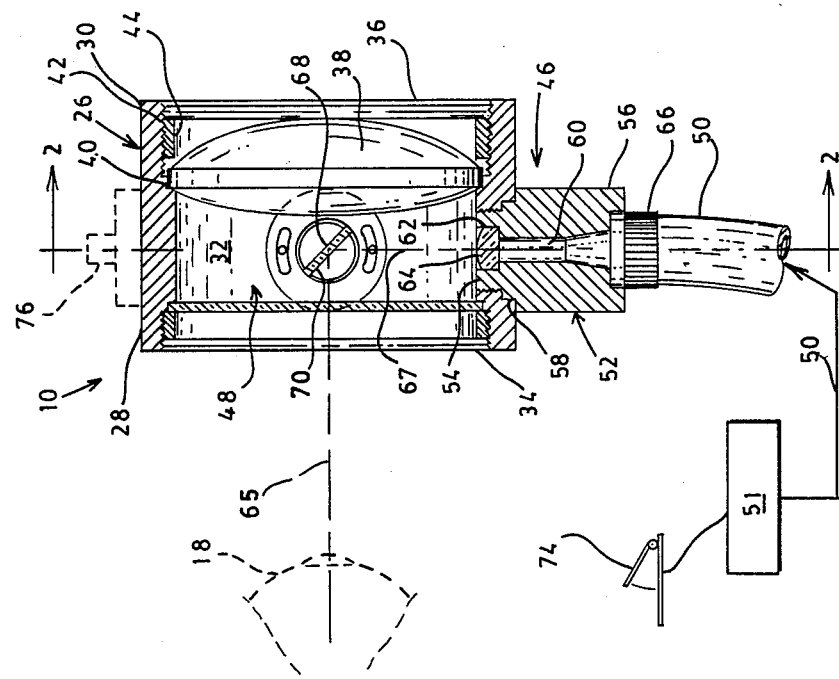
FIG. 2
FIG. 1

OPHTHALMOSCOPE HANDPIECE WITH LASER DELIVERY SYSTEM

DESCRIPTION

1. Technical Field

This invention relates to an ophthalmoscope handpiece with a laser delivery system for viewing the fundus oculi and delivering a remedial laser beam to the fundus. In this particular invention, the handpiece includes a magnifying lens for providing a magnified view of the fundus, and laser delivery means for selectively directing a laser beam to the fundus.

2. Background Art

Ophthalmoscopes have long been used by oculists for viewing the fundus of the eye. Often a binocular indirect ophthalmoscope, which provides a stereoscopic view of the fundus, is used in conjunction with an ophthalmoscope handpiece which contains a magnifying lens which magnifies the oculist's view of the fundus oculi. Such handpieces can be easily positioned to survey the fundus from various angles such that a more comprehensive examination can be made. In addition to their diagnostic applications, in recent years ophthalmoscopes have been used to assist in the targeting of lasers used to correct retinal defects such as detached retinas. For example, U.S. Letters Patent No. 4,477,159 discloses a system which utilizes an ophthalmoscope to assist in the targeting of retinal lesions and which directs a laser beam to the targeted lesion. In such prior art systems, the patient's head is immobilized and a binocular indirect ophthalmoscope is used for viewing the fundus during targeting. The laser is fired from a delivery system mounted on or proximate the binocular ophthalmoscope. However, by locating the laser delivery system on, or proximate, the binocular indirect ophthalmoscope, the mobility of the delivery system is greatly decreased, and targeting of the laser can be difficult and time consuming. Moreover, targeting of lesions located in the periphery of the fundus can be particularly difficult. The system of U.S. Pat. No. 4,477,159 attempts to add mobility by placing the laser delivery means on a binocular indirect ophthalmoscope. However, targeting can still be difficult, particularly due to the inability to bring the delivery means in close proximity to the eye. In this regard, given the great distance between the laser delivery means and the fundus, small movements of the oculist's head or the patient's eye result in large targeting errors. Other related prior art is disclosed by U.S. Letters Pat. Nos. 4,582,405; 4,669,837; 4,669,839; 4,684,227; and 4,699,480.

Therefore, it is an object of the present invention to provide an ophthalmoscope handpiece with a laser delivery system for viewing the fundus oculi and delivering a laser beam to the fundus.

Another object of the present invention is to provide an ophthalmoscope handpiece with laser delivery means which is highly mobile such that laser targeting is more accurate and more easily accomplished.

Yet a further object of the present invention is to provide an ophthalmoscope handpiece which carries a laser delivery means which can be placed in close proximity to the eye so as to reduce targeting errors.

Another object of the present invention is to provide an ophthalmoscope handpiece with a laser delivery system which is inexpensive to manufacture and maintain.

DISCLOSURE OF THE INVENTION

Other objects and advantages will be accomplished by the present invention which provides an ophthalmoscope handpiece for viewing the fundus of the eye and for delivering a laser beam and laser targeting beam to the fundus to effect retinal repairs and for performing other ocular surgical procedures. The handpiece comprises a body having first and second end portions and having a viewing aperture therethrough so as to define a first opening at the first end portion and a second opening at the second end portion. The handpiece is provided with magnifying means, including a magnifying lens mounted in the viewing aperture for providing a magnified view of the fundus. An optical fiber coupling assembly is provided for connecting the handpiece to an optical fiber which communicates a laser targeting beam and a laser beam to the handpiece. The coupling assembly is received in a receptor provided in the body of the handpiece such that the targeting beam and the laser beam are selectively directed into the viewing aperture of the handpiece. Beam deflecting means, mounted within the viewing aperture, selectively intercept the laser beam and targeting beam and redirect the beams through the first opening of the handpiece such that the beams can be directed to the fundus of the eye.

BRIEF DESCRIPTION OF THE DRAWINGS

The above-mentioned features of the present invention will become more clearly understood from the following detailed description of the invention read together with the drawings in which:

FIG. 1 illustrates a side elevation view, in section, of an ophthalmoscope handpiece of the present invention;

FIG. 2 illustrates a front view, in section, of an ophthalmoscope handpiece of the present invention;

BEST MODE FOR CARRYING OUT THE INVENTION

Figure 3:
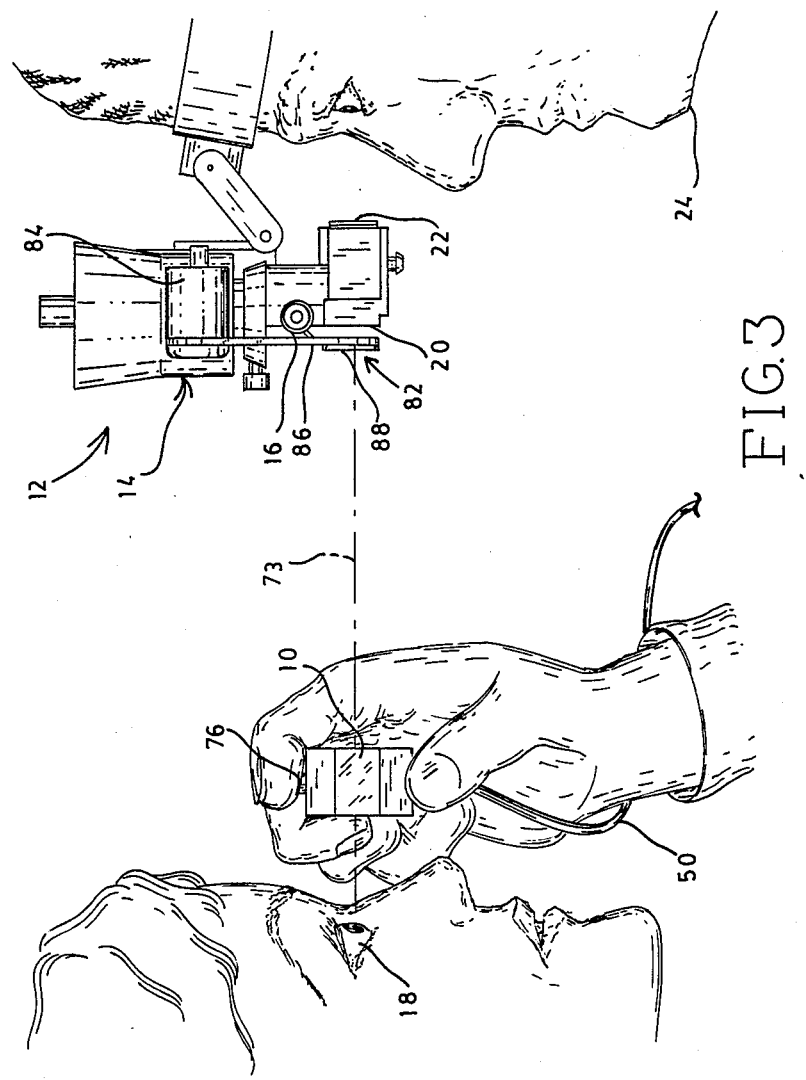
FIG. 3 illustrates a side view of an ophthalmoscope handpiece of the present invention being used by an oculist to examine the fundus of a patient's eye.

An ophthalmoscope handpiece incorporating various features of the present invention is illustrated generally at 10 in the figures. As will be discussed in detail below, the handpiece 10 is used by an oculist to examine the fundus oculi and to target and deliver a laser beam for effecting retinal repairs and for performing other ocular surgical procedures. The handpiece 10 is generally used in conjunction with a binocular indirect ophthalmoscope 12 (See FIGS. 3 and 4) which allows the fundus to be stereoscopically viewed by the oculist. The ophthalmoscope 12 comprises illumination means 14 which directs light through a light aperture 16 and into the eye 18 of the patient through the pupil of the eye. The light is reflected by the fundus and the reflected light is received through the optical aperture 20 of the ophthalmoscope. The reflected light received through the aperture 20 is then directed to a pair of eyepieces 22 by certain mirrors or reflective surfaces (not shown) to be perceived by the oculist 24 in the form of a stereoscopic view of the fundus oculi.

Referring now to FIGS. 1 and 2, the ophthalmoscope handpiece 10 generally comprises a body 26 defining first and second end portions 28 and 30, respectively, and having a viewing aperture 32 therethrough such that first an second openings 34 and 36 are defined at the first and second end portions 28 and 30, respectively. The handpiece 10 further comprises magnifying means which in the preferred embodiment comprises a magnifying lens 38 mounted within the viewing aperture 32. More specifically, the lens 38 is releasably received in a circumferential lens seat 40 provided in the interior walls of the aperture 32, and such interior walls define a threaded portion 42 between the lens seat 40 and the opening 36 for threadably receiving a lens retaining ring 44 which releasably holds the lens 38 in position. Of course, it will be understood that the lens 38 provides the oculist with a magnified view of the fundus to facilitate location of retinal lesions or other defects of the fundus oculi.

The ophthalmoscope handpiece 10 also comprises laser delivery means including an optical fiber coupling assembly 46, and beam deflecting means 48. The coupling assembly 46 serves as a means for connecting the handpiece 10 to an optical fiber 50. The optical fiber 50 is connected to a suitable laser generating means 51 and to a further illumination means 53 which, as will be discussed below, produces a narrow beam of light for targeting the laser beam (See FIG. 1). In the preferred embodiment, the coupling assembly 46 comprises a housing 52 defining first and second end portions 54 and 56, respectively, the first end portion 54 being threadably received in a receptor 58 provided in the body 26. A beam passage 60 extends through the housing 52 from the first end portion 54 to the second end portion 56. Proximate the first end portion 54, the passageway defines a further lens seat 62 for receiving a fiber focusing lens 64, and at the second end portion 54 a fiber optic connector 66 is provided for connecting the optical fiber 50 to the housing 52, thereby placing the passage 60 in communication with the fiber 50. Of course, it will be appreciated by those skilled in the art that the assembly 46 is merely one preferred means for connecting the handpiece 10 to an optical fiber and other suitable means can be used if desired.

As is best illustrated in FIG. 1, the fiber coupling assembly 46 is oriented such that the common path, illustrated at 67, of the laser beam and laser targeting beam, is substantially perpendicular to the axis 65 of the viewing aperture 32. In order to redirect the path of the laser beam and targeting beam to a path substantially coaxial with the aperture 32, the handpiece 10 is provided with the above-referenced beam deflection means 48. In the preferred embodiment, the deflection means 48 comprises a transparent member 68 pivotally mounted in the handpiece 10 so as to bisect the viewing aperture 32. The transparent member 68 defines a forward surface 70 carrying a centrally disposed reflective surface portion 72 which intercepts the targeting beam and the laser beam at, or proximate, the axis of the aperture 32. As illustrated in FIG. 1, the transparent member 68 is pivotally secured at its opposite ends to the body 26 of the handpiece 10 such that the reflective surface portion 72 can be positioned at substantially a forty-five (45) degree angle to the axis of the aperture 32 such that the targeting and laser beams are redirected to a path substantially coaxial with the aperture 32. Of course, the pivotal mounting of the transparent member 68 allows the angle of the reflective surface portion 72 to be adjusted and, thus, the exit path of the laser and targeting beams to be adjusted. Further, it will be noted that the transparent member 68, with its reflective surface portion 72, merely represents one preferred beam deflection means, and it is contemplated that other suitable means can be utilized for redirecting the laser and laser targeting beams if desired.

Figure 4:
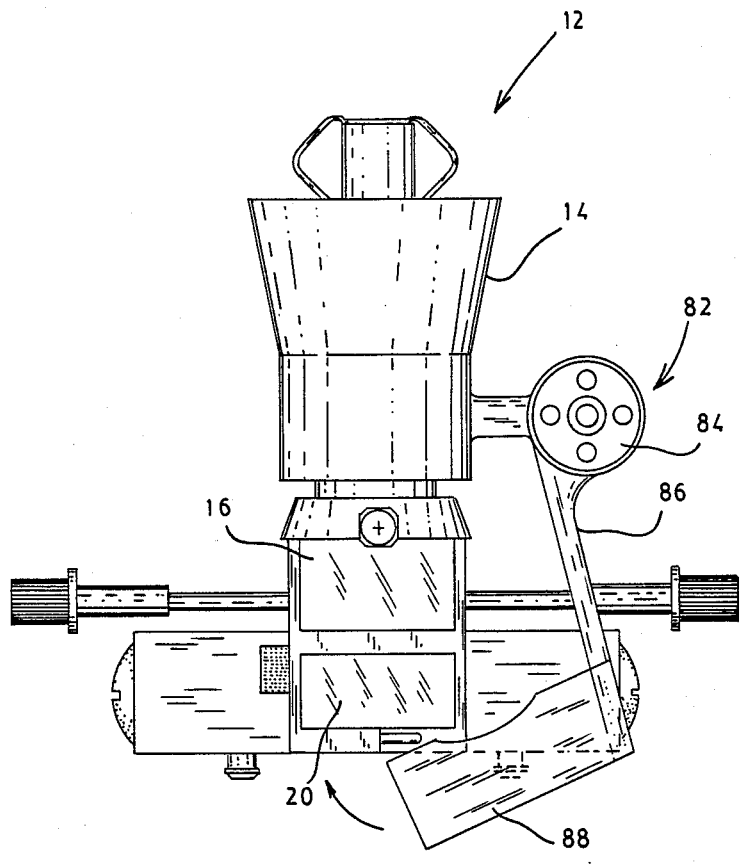
FIG. 4 illustrates a front view of a binocular indirect ophthalmoscope filter means of the present invention.

Referring now to FIGS. 1 and 3, when in use, the handpiece 10 is held in front of the patient's eye 18 and with the aid of the binocular ophthalmoscope 12, the oculist 24 views (along sight line 73) the fundus through the magnifying lens 38 of the handpiece 10, with the illumination means 14 of the binocular ophthalmoscope 12 providing the necessary illumination for viewing. As the oculist 24 surveys the fundus, the narrow targeting beam generated by the further illumination means 53, and communicated to the handpiece 10 by the fiber 50, reflects off of the fundus so as to provide an illuminated spot on the fundus where the laser beam will strike when fired. Accordingly, the laser is targeted by manipulating the handpiece 10 to place the illuminated spot produced by the targeting beam at the location at which laser impact is desired. When targeting is accomplished, the laser is fired by a suitable laser actuating means such as the foot pedal 74 (See FIG. 1). Of course, it will be appreciated that where the actuator means for firing the laser is remote from the handpiece 10, there is a risk that the laser can inadvertently be fired when the handpiece is not under proper control, or before the targeting has been accomplished. In order to obviate such inadvertent firing, the handpiece can optionally be provided with a safety switch 76, connected to the laser generating means 51 by conventional circuitry, which must be manually depressed, or otherwise actuated by the oculist, before the laser actuator means, i.e., the pedal 74, will fire the laser.

It will be appreciated by those skilled in the art that when the laser is fired, a portion of the light generated is reflected by the fundus. Therefore, in order to protect the oculist's eyes from damage due to reflection of the laser beam, in the preferred embodiment, a filter means 82 is provided for mounting on the binocular ophthalmoscope 12 to filter out laser reflection. The filter means 82 comprises a filter actuator 84 secured to the ophthalmoscope 12 and provided with a pivoting actuator arm 86 which carries a filter panel 88. The actuator 84 is connected by conventional circuitry, including switching means, to the laser generating means 51 such that as the foot pedal 74 is depressed, the actuator 84 pivots the actuator arm 86 so as to place the filter panel 88 in front of the optical aperture 20 of the ophthalmoscope 12. And, only when the filter panel 88 is in place in front of the aperture 20 does the switching means allow the laser to fire.

In light of the above, it will be appreciated that the ophthalmoscope handpiece 10 with its laser delivery system provides great advantages over the prior art. The laser delivery system is highly mobile, and, in fact, can be wielded by the oculist much like a scalpel. Also, the ability to bring the point of laser delivery in close proximity to the patient's eye enhances targeting accuracy and allows better access to the periphery of the fundus.

While a preferred embodiment has been shown and described, it will be understood that there is no intent to limit the invention to such disclosure, but rather it is intended to cover all modifications and alternate constructions falling within the spirit and scope of the invention as defined in the appended claims.

We claim:

1. An ophthalmoscope handpiece for viewing the fundus of the eye and for selectively delivering a laser beam and a laser targeting beam to said fundus, said laser beam being generated by laser generating means provided with an actuator for firing said laser, said laser beam and said laser targeting beam being communicated to said handpiece by an optical fiber, said ophthalmoscope handpiece comprising:

a body having first and second end portions and defining a viewing aperture therethrough so as to define a first opening at said first end portion and a second opening at said second end portion, said body being further provided with a third opening accessing said viewing aperture, said third opening defining a threaded receptor;

magnifying means, including a magnifying lens mounted in said viewing aperture at a position intermediate said second opening and said third opening for providing a magnified view of said fundus;

a fiber coupling assembly for connecting said optical fiber to said handpiece whereby said laser and said laser targeting beam are communicated through said third opening into said viewing aperture, said coupling assembly including a housing having a first threaded end portion and a second end portion, and defining a beam passage therethrough from said first end portion of said housing to said second end portion of said housing, said first end portion of said housing being threadably received by said receptor of said body so as to place said beam passage in communication with said viewing aperture, said second end portion of said housing being provided with a fiber optic connector for connecting said optical fiber in communication with said beam passage, said coupling assembly further comprising a fiber focusing lens mounted within said beam passage proximate said first end portion of said housing for focusing said laser beam, whereby said laser beam and said laser targeting beam selectively enter said viewing aperture on a first path; and beam deflecting means including a transparent member pivotally mounted in said viewing aperture, said transparent member defining a forward surface provided with a reflective surface portion for intercepting said laser beam and said laser targeting beam on said first path and redirecting said laser beam and said laser targeting beam to a second path exiting said viewing aperture through said first opening of said body to thereby deliver said laser beam and said laser targeting beam to said fundus.

2. The ophthalmoscope handpiece of claim 1 wherein said handpiece is provided with a safety switch mounted on the exterior of said body and connected by circuitry means to said laser generating means whereby said laser can be fired only when said switch is actuated.

3. The ophthalmoscope handpiece of claim 2 wherein said viewing aperture is defined by interior walls, said interior walls defining a circumferential lens seat for receiving said magnifying lens and a threaded portion between said lens seat and said second opening for threadably receiving a lens retaining ring whereby said magnifying lens is releasably secured in said lens seat.

4. An ophthalmoscope handpiece system for viewing the fundus of the eye and for selectively delivering a laser beam and a laser targeting beam to said fundus, said laser beam being generated by laser generating means provided with an actuator for firing said laser, said laser beam and said laser targeting beam being communicated to said handpiece system by an optical fiber, said handpiece system comprising:

an ophthalmoscope handpiece, said handpiece including a. a body having first and second end portions and defining a viewing aperture therethrough so as to define a first opening at said first end portion and a second opening at said second end portion through which said fundus is viewed, said body further defining a third opening accessing said viewing aperture, b. magnifying means, including a magnifying lens mounted in said viewing aperture at a position intermediate said second opening and said third opening for providing a magnified view of said fundus, c. a fiber coupling assembly for connecting said optical fiber to said handpiece whereby said laser beam and said laser targeting beam are selectively communicated through said third opening of said body and into said viewing aperture so as to define a first beam path, and d. beam deflecting means mounted within said viewing aperture for intercepting said laser beam and said laser targeting beam, and redirecting said laser beam and laser targeting beam to a second beam path so as to direct said laser beam and laser targeting beam through said first opening to thereby direct said laser beam and laser targeting beam to said fundus;

a binocular indirect ophthalmoscope for providing a stereoscopic view of said fundus through said viewing aperture of said handpiece, said binocular indirect ophthalmoscope having an optical aperture for receiving light reflected from said fundus;

filtering means for prohibiting reflection of said laser beam off of said fundus from entering said optical aperture, said filter means including an actuator mounted on said binocular indirect ophthalmoscope, said actuator having an actuator arm carrying a filter panel, whereby said actuator pivots said actuator arm to bring said filter panel between said fundus and said optical aperture in response to activation of said actuator of said laser generating means and before the firing of said laser beam.

5. An ophthalmoscope handpiece for viewing, in combination with a binocular indirect ophthalmoscope, the fundus of the eye and for delivering a laser beam to said fundus, said laser beam being communicated to said handpiece by an optical fiber, said ophthalmoscope handpiece comprising:

a body having first and second end portions and having a viewing aperture therethrough so as to define a first opening at said first end portion and a second opening at said second end portion, said viewing aperture having a line of sight from said first end portion to said second end portion, said body defining a third opening accessing said viewing aperture;

magnifying means, including a magnifying lens, mounted in said viewing aperture and intercepting said line of sight for providing a magnified view of said fundus;

a fiber coupling assembly for connecting said optic fiber to said handpiece whereby said laser beam is selectively communicated through said third opening of said body and into said viewing aperture; and beam deflecting means mounted within said viewing aperture, said beam deflecting means including a transparent member pivotally mounted in said viewing aperture and intercepting said line of sight, said transparent member defining a forward surface provided with a reflective surface portion for intercepting said laser beam as said laser beam is directed into said viewing aperture and redirecting said laser beam through said first opening of said body toward said fundus of said eye.

6. An ophthalmoscope handpiece for viewing the fundus of the eye and for delivering a laser beam to said fundus, said laser beam being communicated to said handpiece by an optical fiber, said ophthalmoscope handpiece comprising:

a body having first and second end portions and having a viewing aperture therethrough so as to define a first opening at said first end portion and a second opening at said second end portion, said body further defining a third opening accessing said viewing aperture;

magnifying means, including a magnifying lens, mounted in said viewing aperture for providing a magnified view of said fundus;

a fiber coupling assembly for connecting said optical fiber to said handpiece whereby said laser beam is selectively communicated through said third opening of said body and into said viewing aperture; and beam deflecting means mounted within said viewing aperture for intercepting said laser beam and directing said laser beam through said first opening of said body, said beam deflecting means having a transparent member pivotally mounted in said viewing aperture, said transparent member defining a forward surface provided with a reflective surface portion for intercepting said laser beam as said beam is directed into said viewing aperture and redirecting said laser beam through said first opening of said body.

7. An ophthalmoscope handpiece for viewing the fundus of the eye and for delivering a laser beam to said fundus, said laser beam being communicated to said handpiece by an optical fiber, said ophthalmoscope handpiece comprising:

a body having first and second end portions and having a viewing aperture therethrough so as to define a first opening at said first end portion and a second opening at said second end portion, said body further defining a third opening accessing said viewing aperture;

magnifying means, including a magnifying lens, mounted in said viewing aperture for providing a magnified view of said fundus;

a fiber coupling assembly cooperating with said third opening, said fiber coupling assembly including a housing having a first end portion and a second end portion and defining a beam passage therethrough from said first end portion of said housing to said second end portion of said housing, said first end portion of said housing engaging said body at said third opening whereby said beam passage is placed in communication with said viewing aperture, said second end portion of said housing being provided with a fiber optic connector for connecting said optical fiber to said housing and placing said optical fiber in communication with said beam passage, said coupling assembly further comprising a fiber focusing lens mounted within said beam passage for focusing said laser beam whereby said laser beam enters said viewing aperture on a first path; and beam deflecting means mounted within said viewing aperture, said beam deflecting means having a transparent member pivotally secured at its opposite end portions to said body so as to substantially bisect said viewing aperture, said transparent member defining a forward surface provided with a centrally disposed reflective surface portion for intercepting said laser beam as said laser beam enters said viewing aperture on said first path and redirecting said laser beam to a second path so as to exit said viewing aperture through said first aperture of said body to thereby deliver said laser beam to said fundus.

* * * * *